(12) United States Patent
Sheth et al.

(10) Patent No.: US 7,861,777 B2
(45) Date of Patent: Jan. 4, 2011

(54) VISCOMETER FOR DOWNHOLE PUMPING

(75) Inventors: Ketankumar K. Sheth, Tulsa, OK (US); John L. Bearden, Claremore, OK (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 12/191,931

(22) Filed: Aug. 14, 2008

(65) Prior Publication Data

US 2009/0044953 A1 Feb. 19, 2009

Related U.S. Application Data

(60) Provisional application No. 60/956,047, filed on Aug. 15, 2007.

(51) Int. Cl.
*E21B 43/12* (2006.01)
(52) U.S. Cl. .................................. 166/250.15
(58) Field of Classification Search ............ 166/250.15, 166/369, 105
See application file for complete search history.

(56) References Cited

U.S. PATENT DOCUMENTS

| | | | |
|---|---|---|---|
| 5,458,200 A | 10/1995 | Lagerlef | |
| 6,092,598 A | 7/2000 | Breit | |
| 6,206,093 B1 | 3/2001 | Lee et al. | |
| 6,543,281 B2 | 4/2003 | Pelletier et al. | |
| 6,564,874 B2 | 5/2003 | Narvaez | |
| 6,631,762 B2 | 10/2003 | Collette | |
| 6,755,079 B1 | 6/2004 | Proett et al. | |
| 6,990,851 B2 * | 1/2006 | Spaid et al. | 73/54.13 |
| 7,114,557 B2 | 10/2006 | Cudmore et al. | |
| 7,219,537 B2 | 5/2007 | Andle | |
| 7,222,671 B2 | 5/2007 | Caudwell et al. | |
| 7,231,973 B2 * | 6/2007 | Sloan | 166/252.5 |
| 7,434,457 B2 | 10/2008 | Goodwin et al. | |
| 2005/0034872 A1 | 2/2005 | Gay et al. | |
| 2007/0215346 A1 * | 9/2007 | Sloan et al. | 166/250.01 |

OTHER PUBLICATIONS

Fotos, Peleties and Trusler, J.P. Martin, Advanced Fluid Property Measurement and Prediction for Oilfield Applications, http://aiche.confex.com/aiche/2006/preliminaryprogram/abstract_62749.htm, Jul. 27, 2007 (3 pages).
Gusler, William, et al., Paper No. 990009-PA, A New Extreme-HP/HT Viscometer for New Drilling-Fluid Challenges, http://www.spe.org/elibrary/servlet/spepreview?print=print&showSPEFavorites=false&titl..., Jul. 7, 2007 (2 pages).
Written Opinion of the International Searching Authority dated Jan. 8, 2009, 5 pages.
International Search Report dated Jan. 8, 2009, 3 pages.

* cited by examiner

*Primary Examiner*—Kenneth Thompson
*Assistant Examiner*—Catherine Loikith
(74) *Attorney, Agent, or Firm*—Bracewell & Giuliani LLP

(57) ABSTRACT

A submersible pumping system for use downhole, wherein the system includes a pump, an inlet section for receiving fluid, a pump motor, and a viscometer. Pumping system operating parameters are adjusted based on wellbore fluid viscosity measured by the viscometer. The viscometer can be disposed deep in the wellbore, adjacent the pump, seal, motor, at the pump intake or anywhere on the pumping system. The viscometer may be connected to a control system for controlling the pumping system in response to viscosity measurement and may include a sonic viscometer. A method of operating a downhole submersible pumping system is included that measures fluid viscosity in the wellbore during production operations. Pumping parameters can be adjusted based on the measured viscosity.

12 Claims, 6 Drawing Sheets

VISCOMETER FOR DOWNHOLE PUMPING

RELATED APPLICATIONS

This application claims priority to and the benefit of U.S. Provisional Application Ser. No. 60/956,047, filed Aug. 15, 2007, the full disclosure of which is hereby incorporated by reference herein.

BACKGROUND

1. Field of Invention

The present disclosure relates to downhole pumping systems submersible in well bore fluids. More specifically, the present disclosure concerns monitoring viscosity of fluid flowing to a downhole pump and adjusting pump operating parameters depending on the viscosity measurement.

2. Description of Prior Art

Submersible pumping systems, as a means of artificial lift method, are often used in hydrocarbon producing wells for pumping fluids from within the well bore to the surface. These fluids are generally liquids and include produced liquid hydrocarbon as well as water. One type of system used in this application employs an electrical submersible pump (ESP), another example of artificial lift method is a positive cavitation pump (PCP) system. ESPs are typically disposed at the end of a length of production tubing and have an electrically powered motor. Often, electrical power may be supplied to the pump motor via cable or wireline. Typically, the pumping unit is disposed within the well bore just above where perforations are made into a hydrocarbon producing zone. This placement thereby allows the produced fluids to flow past the outer surface of the pumping motor and provide a cooling effect.

With reference now to FIG. 1, an example of a submersible ESP disposed in a well bore is provided in a partial cross sectional view. In this embodiment, a downhole pumping system 7 is shown within a cased wellbore 5. The pumping system 7 is suspended within the wellbore 5 on production tubing 11. The downhole pumping system 7 comprises a pump section 12, a seal section 16, and a motor 18. The seal section 16 forms an upper portion of the motor 18 and is used for equalizing lubricant pressure in the motor 18 with the wellbore hydrostatic pressure. Energizing the motor 18 then drives a shaft (not shown) coupled between the motor 18 and the pump section 12. Impellers are coaxially disposed on the shaft and rotate with the shaft within respective diffusers formed into the pump 12.

Centrifugal action of the impellers produces a localized reduction in pressure in the diffuser thereby inducing fluid flow into the diffuser. In this embodiment, a series of inlets 14 are provided on the pump housing 10 wherein formation fluid can be drawn into the inlets and into the pump section 12. The series of inlets 14 can be an integral part of the pump or a separate intake/gas separator. The source of the formation fluid, which is shown by the arrows, are perforations 22 formed through the casing 6 of the wellbore 5 and into a surrounding hydrocarbon producing formation 20. Thus the fluid flows from the formation 20, past the motor 18 on its way to the inlets 14. The flowing fluid contacts the housing of the motor 18 and draws heat from the motor 18, providing cooling to the motor 18.

In spite of the heat transfer between the fluid and the motor 18, over a period of time the motor 18 may become overheated. This is especially a problem when the fluid has a high viscosity, a low specific heat, and a low thermal conductivity. This is typical of highly viscous crude oils. The motor 18 may be forced to operate at an elevated temperature, past its normal operating temperature, in order to reject the internally generated heat. This temperature upset condition can reduce motor life and results in a reduction in operational times of the pumping system.

Pump horsepower and torque requirements increase with the increase in the viscosity of the fluid. When ESP system pumps highly viscous fluid, the increase in horsepower requirements leads to higher torque and overloading of the motor 18. This may result in breaking of shaft of the pump and/or the motor, as well as additional heat generation in the motor.

SUMMARY OF INVENTION

The present disclosure includes a downhole submersible pumping system, as a means of artificial lift method, for use in a cased wellbore comprising, a pump, a seal, and a motor coupled to the pump; and a viscometer for measuring fluid flow. The viscometer can be disposed deep in the wellbore, adjacent the pump, seal, motor, at the pump intake or anywhere on the ESP system. The viscometer may be connected to a control system for controlling the pumping system in response to viscosity measurement. The viscometer may comprise a sonic viscometer.

Also disclosed herein is a method of operating a downhole submersible pumping system by measuring fluid viscosity in the wellbore during downhole production pumping operations. The method may further comprise adjusting pumping parameters based on the measured viscosity. The viscosity may be measured at the wellbore bottom, along the pump motor, and at the pump inlet.

BRIEF DESCRIPTION OF DRAWINGS

Some of the features and benefits of the present invention having been stated, others will become apparent as the description proceeds when taken in conjunction with the accompanying drawings, in which.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The present invention will now be described more fully hereinafter with reference to the accompanying drawings in which embodiments of the invention are shown. This invention may, however, be embodied in many different forms and should not be construed as limited to the illustrated embodiments set forth herein; rather, these embodiments are provided so that this disclosure will be thorough and complete, and will fully convey the scope of the invention to those skilled in the art. Like numbers refer to like elements throughout.

The present disclosure provides embodiments of a downhole submersible pumping system, as a means of artificial lift method, for producing fluids from within a wellbore up to the surface. More specifically, the downhole submersible pumping system described herein includes a viscometer for measuring wellbore fluid. A progressive cavity pump system and other artificial lift methods can be used in similar way as ESP systems for producing well fluids and this concept can be easily applied to other artificial lift methods.

Figure 1:
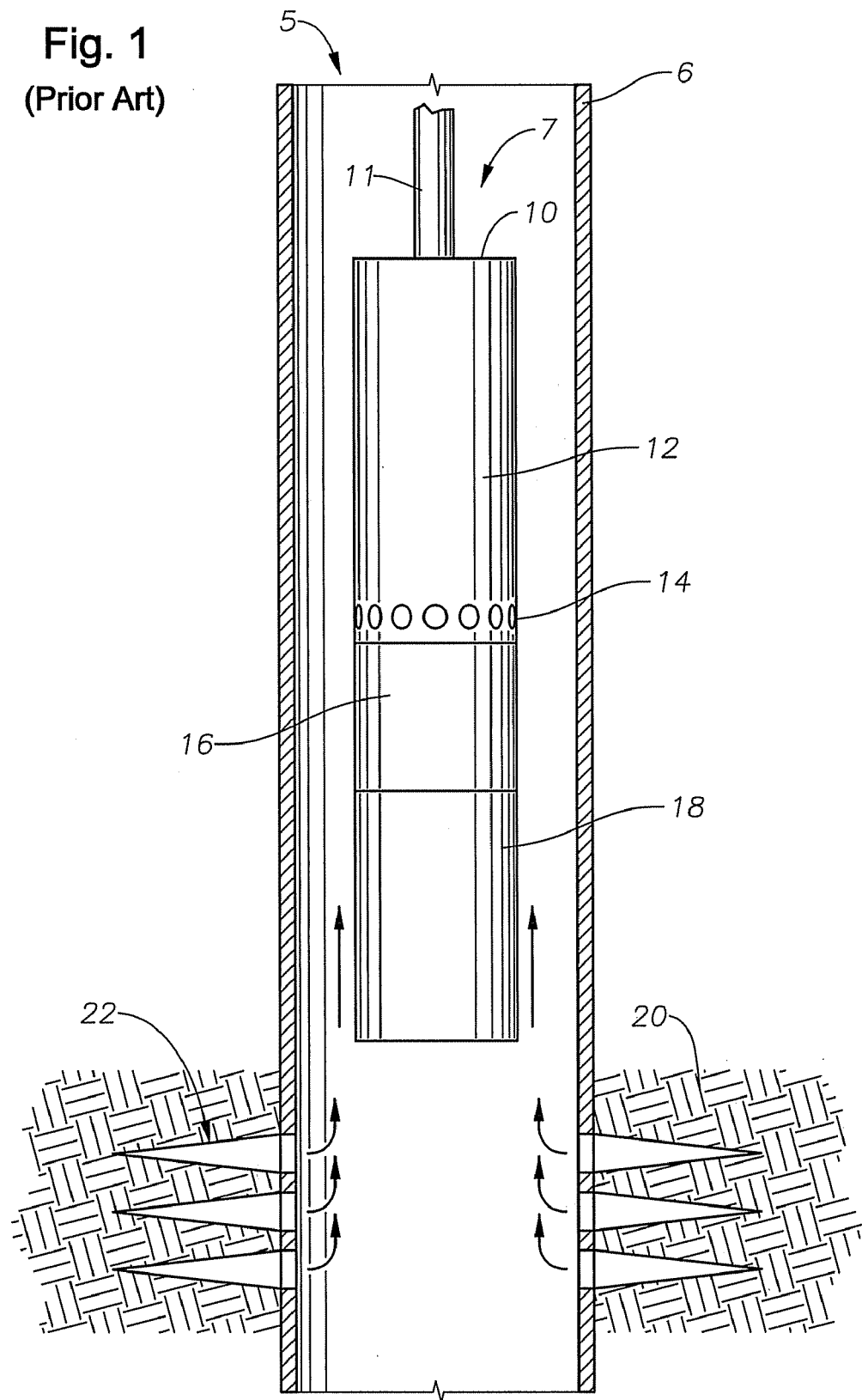
FIG. 1 shows a prior art downhole submersible system shown in a partial cross sectional view.
Figure 2:
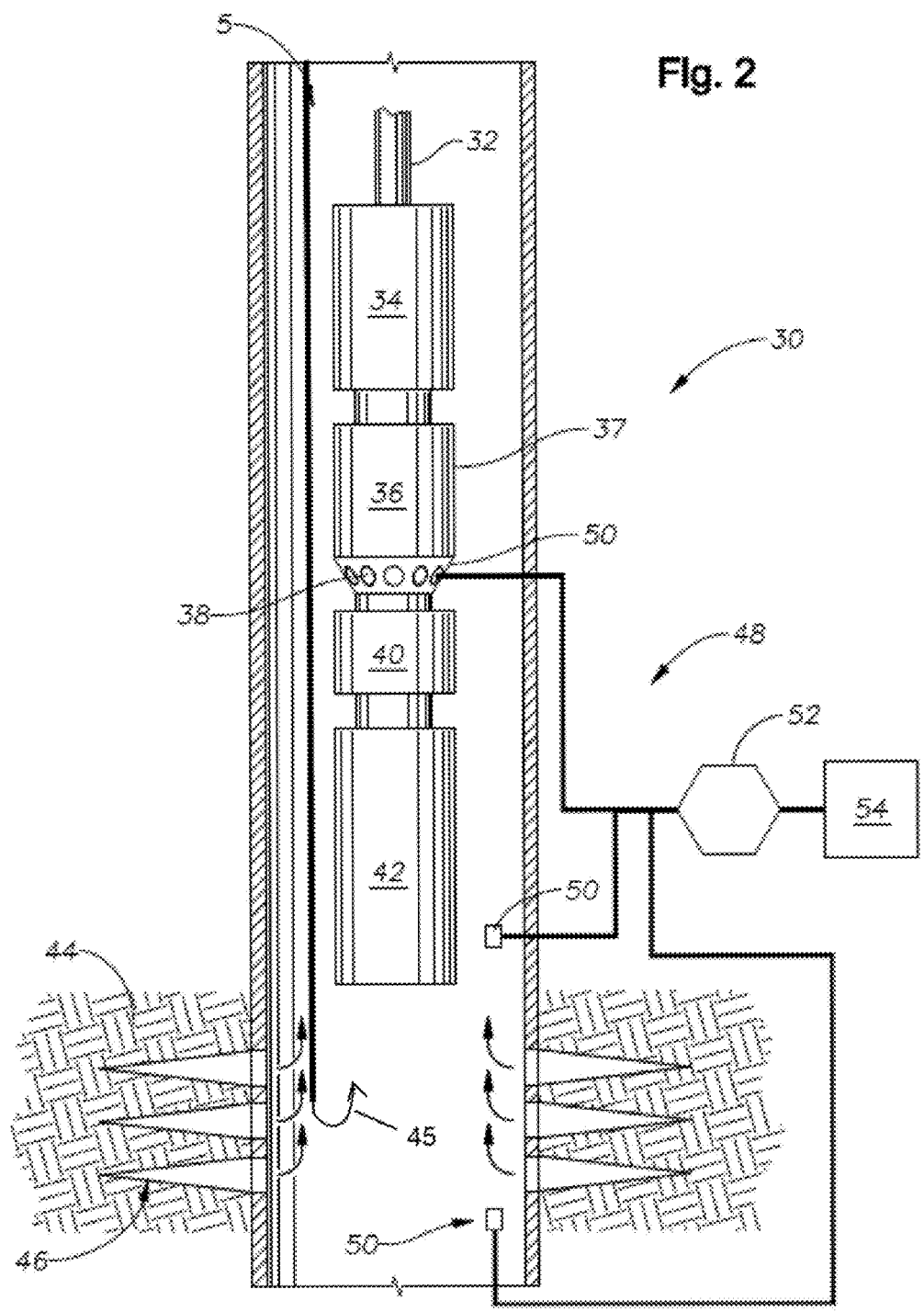
FIG. 2 shows a side view of an embodiment of a pumping system in accordance with the present disclosure disposed within a cased well bore.

FIG. 2 provides a side view of a pumping system disposed within a cased wellbore. The pumping system 30, also referred to herein as an electrical submersible pumping system, is within a cased wellbore 5 disposed on production tubing 32. In the embodiment shown, the pumping system 30 comprises a pumping system housing 37, a motor 42, a seal section 40, an optional intake/gas separator 36, and a pump section 34. Inlets 38 are provided on the separator 36 that provide a fluid flow path to the pump section 34. If the optional separator 36 is not included with the pumping system 30, the inlets 38 may instead be provided on the pump section 34.

The pump section 34 comprises a housing covering a pump mechanically coupled to the electrically powered motor 42 via a shaft (not shown). The pump size and capacity is dependent upon the particular application it will be used in. The seal section 40 may be included with the pumping system 30 disposed on the upper portion of the motor 42 in a coaxial fashion. The seal section 40 may be included for equalizing hydrostatic pressure of the well fluid with internal fluids within the system 30, such as the lubricant used within the motor 42.

The optional gas separator 36 is used for removing any gas that may be entrained in the fluid flowing to the pump. Allowing gas to a pump inlet can lock the pump and prevent fluid flow or can damage a pump's internal components, such as its impellers. The gas separator 36 discharges into the wellbore 5 that surrounds the pump system 30. The pump, which is coaxially disposed on the upper portion of the separator 36, can be any type of pump in multi sections, used for pumping wellbore fluids up an associated production tubing 32 and to the wellbore surface.

The production fluid in the wellbore 5 is illustrated by arrows emanating from perforations 46. These perforations are shown laterally extending from the cased wellbore 5 and into the hydrocarbon producing formation 44 that surrounds a portion of the wellbore. As discussed above, the fluid flows past the motor 42 on its way to the pump inlet 38. The fluid flowing passed the motor 42 provides a cooling effect, thus changes or variations in fluid properties can have a noticeable effect on pump cooling A measurement/control system 48, shown in schematic view, is provided along with the electrically submersible pumping system 30 of FIG. 2. The control system 48 includes a monitor/processor 52, a controller 54, and viscometers 50. The controller 54, which may comprise an information handling system (IHS) or a microprocessor, is shown in electrical communication with the monitor/processor 52. Based upon data signals from the monitor/processor 52, the controller 54 may be configured to correspondingly control operation of the pumping system 30. Pumping system control may include controlling power, such as electrical power, to the pumping system 30 and/or motor 42, as well as adjusting motor 42 and pump speed.

FIG. 2 illustrates viscometers 50 located (1) below the motor 42; (2) adjacent the motor 42; and (3) proximate/within a fluid inlet 38. However other embodiments of the present invention exist having a single viscometer in one of the above cited locations, or multiple viscometers well in excess of the number shown in FIG. 2. The type of viscometer for use in the present invention is not limited to a particular type or types of meters. Viscometer embodiments include a sonic viscometer, a concentric cylinder, vibrating wire, micro-electro-mechanical system, shear mode piezoelectric transducer, a venturi type with pressure measurement, vibrating cavity, and those employing magnetic fields. A sonic viscometer works on acoustic viscosity, which is a third type of viscosity measurement system. Generally used viscosity measurements are kinematic and dynamic viscosity; where kinematic viscosity is equal to the absolute value of viscosity/density; acoustic viscosity is also a product of absolute viscosity and density. This method may optionally employ a shear acoustic wave resonator. The loading of the acoustic resonator caused by viscous fluid depends upon the viscosity and density of the fluid. Knowing the loading on the resonator and density of the viscous fluid, a viscosity value can be obtained. Viscometers for use with the present invention can be obtained from Vectron, 267 Lowell Road, Hudson N.H., 03051; ph: 1-888-382-7661.

In one mode of operation, viscosity rates or values from one or more of the viscometers 50 are relayed to the monitor/processor 52 via electrical leads as control links. One optional embodiment of control links includes using telemetry to relay viscosity rates; examples of telemetry include mud pulses, and radio frequency waves. Although the measurement/control system 48 displayed in FIG. 2 is outside of the cased wellbore 5, all or a portion of the measurement/control system 48 may be within the wellbore 5, the measurement/control system 48 may be affixed to the pumping system 30 or within its housing. Optionally, one or more of the elements of the measurement/control system 48 may be at the surface.

The monitor/processor 52 may be programmable (or configured) to send appropriate signals to the controller 54 based upon the signal it receives from a viscometer 50. For example, should a high viscosity be measured by a viscometer 50, the monitor/processor 52 might have commands programmed for adjusting the electrical load delivered to the motor 42. A control link, such as an electrical lead, may provide communication between the processor 52 and the motor 42. Optionally, the processor 52 may be in communication to the electrical power supplied to the motor 42 for controlling the amount of power delivered to the motor 42. It is well within the capabilities of those skilled in the art to determine proper adjustments to the pumping system 30 based upon a value of a fluid viscosity measured within the wellbore.

Monitoring fluid viscosity is also useful in controlling corrosion. Knowledge of viscosity along with chemical state of the fluid can provide a basis for protecting the pumping system from corrosion by adding corrosion inhibitor into the fluid. The basis to determine the addition of a proper amount of corrosion inhibitor into the fluid can also be determined from knowing a viscosity value. Additionally, viscosity values are useful in determining any values of water breakout. With breaking out of water, an emulsion may be formed increasing mixture viscosity. A change in downhole fluid viscosity can also indicate when wax and/or gas has separated from the wellbore fluid. Having a monitored viscosity value, those skilled in the art can determine an adequate amount of corrosion inhibitor 45 to add and also determine values of water breakout without undue experimentation. Thus the present disclosure includes methods of adding/adjusting corrosion inhibitor 45 to fluid, determining water breakout, and monitoring wax and/or gas separation from wellbore fluid; all based on measuring fluid viscosity downhole. The system and method of the present disclosure also includes measuring viscosity changes from hydrocarbon production enhancement measures, such as water injection into the reservoir.

Figure 3:
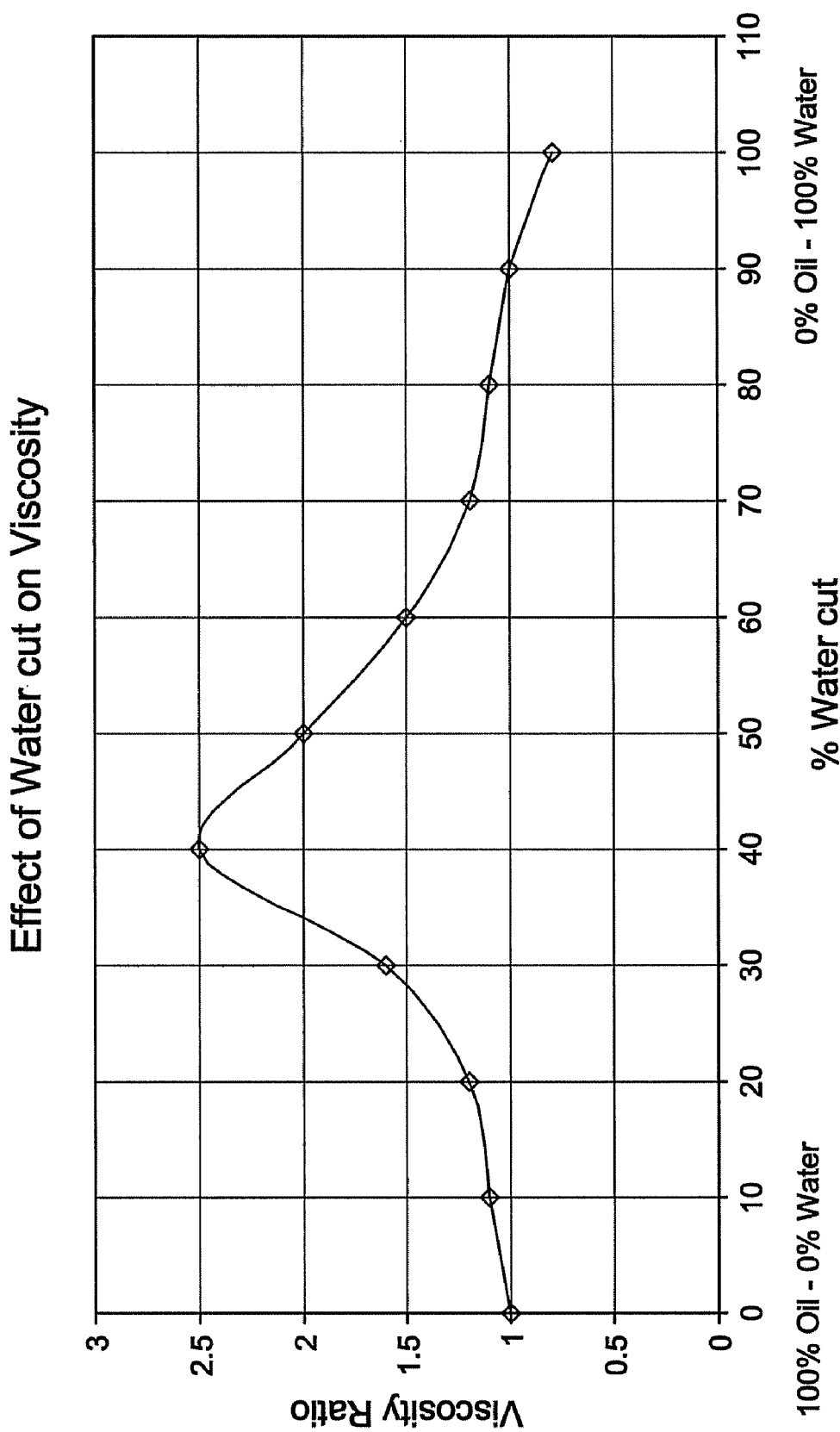
FIG. 3 graphically depicts fluid viscosity based on water percentage content.

FIG. 3 graphically illustrates an example of how injected water can alter the viscosity of produced fluid. In the example provided in FIG. 3, the produced fluid (or mixture) viscosity is at its greatest during 30 percent to 60 percent of water cut (percent by volume). However due to the many variables inherent in downhole hydrocarbons, the values illustrated in FIG. 3 depend on the hydrocarbon properties and downhole conditions. Generally the wellbore fluid initially comprises all hydrocarbons with a gradual increase in water percentage over time. Knowing real time production fluid operational conditions, pump speed can be adjusted to account for measured fluid property changes.

Wellbore fluid flowing past the motor can provide cooling to the motor. However, the fluid flowing adjacent the motor can change between laminar and turbulent flow regimes based on changes in fluid viscosity. Since heat transfer rates vary depending on the fluid flow regime, realtime operational fluid viscosity measurements provide accurate fluid to pump motor heat transfer values. This in turn enables accurate motor temperature estimates in spite of changing fluid flow regime changes. If the motor temperature approaches an undesirably high temperature, operational conditions may be adjusted to lower motor temperature. The heat transfer between the motor and fluid at different flows can be modeled as well as motor temperature from controlling power input. For example, electrical loading to the motor may be adjusted in response to a derived value of motor temperature.

The torque required for starting a pump is dependent on the wellbore fluid viscosity. Thus, knowledge of fluid viscosity prior to initiating the pump can provide guidelines for pump start up. If wellbore fluid viscosity exceeds a typical wellbore fluid viscosity, based on this information, required torque and BHP can be calculated. If the calculated requirement surpasses the motor and pump capacity, the starting RPM may be changed and the ratio of operating speed to design speed can be increased to avoid failure.

Figure 4:
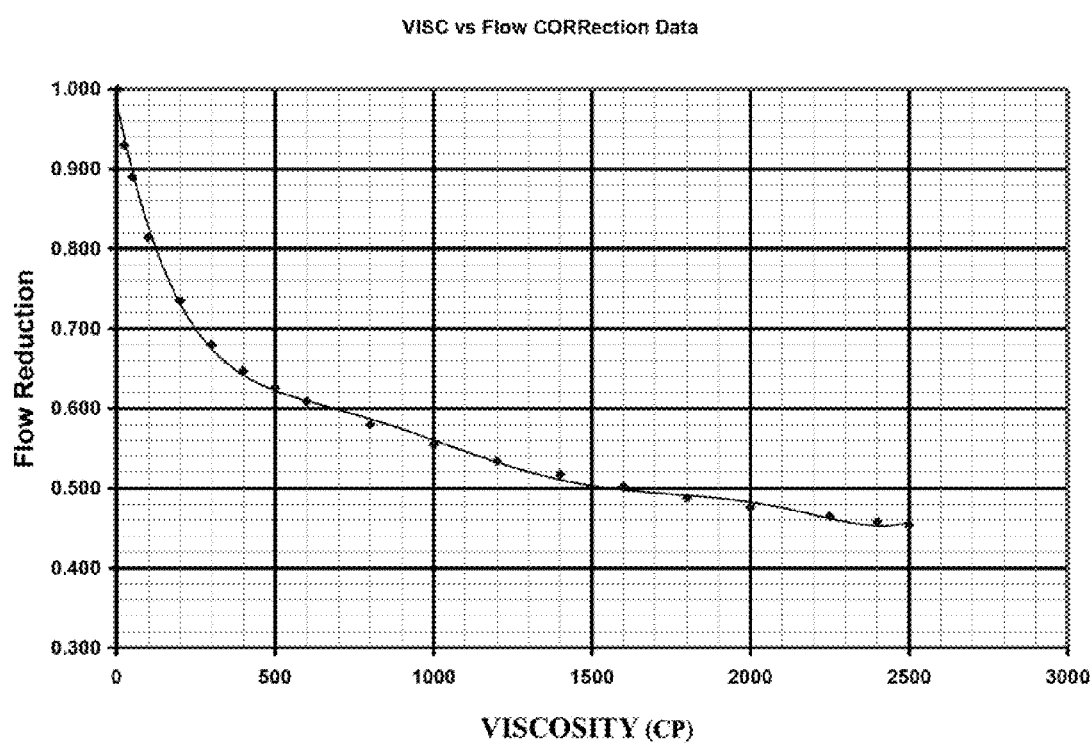
FIG. 4 is a graph illustrating how viscosity affects flow.
Figure 5:
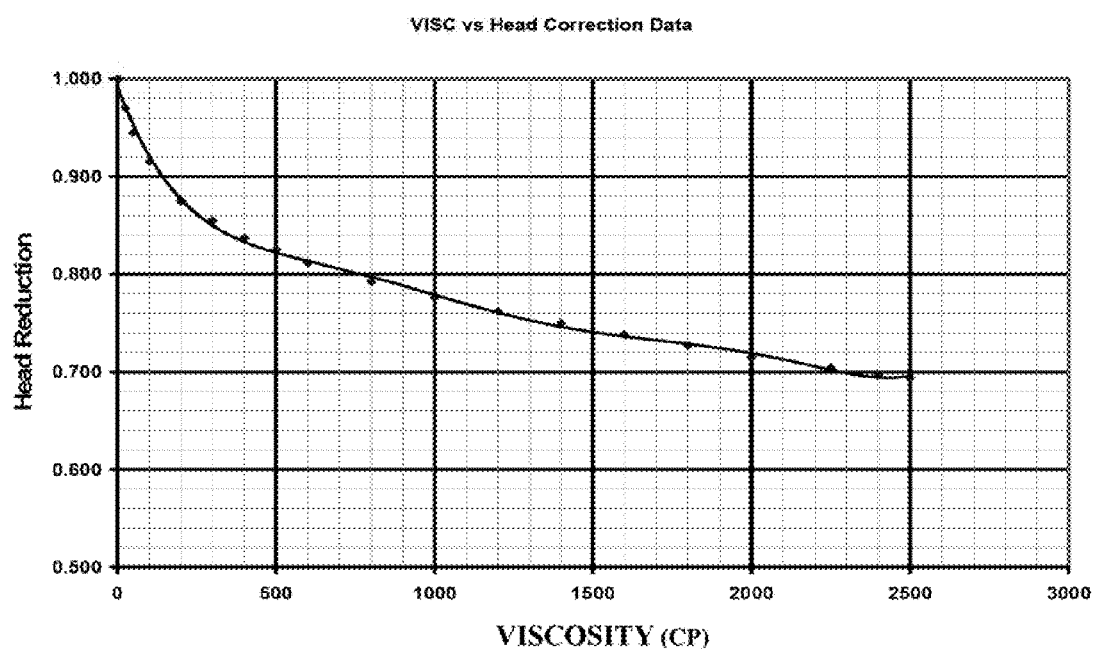
FIG. 5 graphically portrays how viscosity affects pump head.
Figure 6:
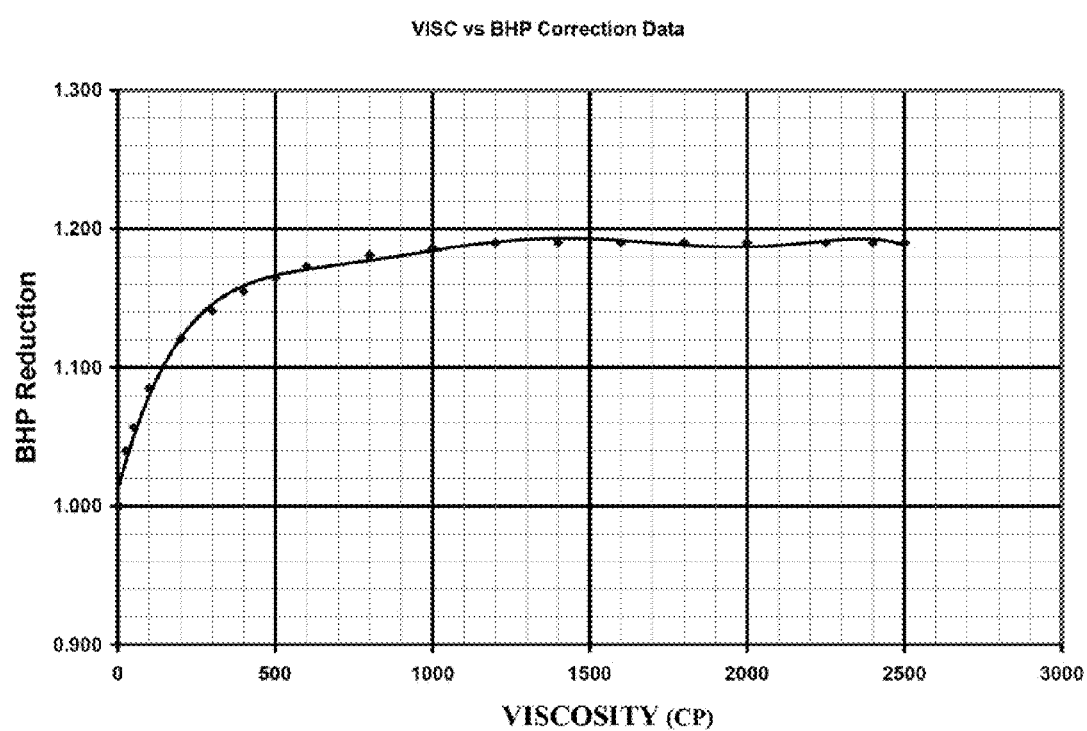
FIG. 6 is a graph relating Brake Horsepower requirements and viscosity.

FIGS. 4 through 6 graphically illustrate viscosity effects on production operations. FIG. 4 illustrates an example of how increasing viscosity reduces fluid flow due to increased resistance to flow. For example, assuming 100% flow at a corresponding viscosity of 0 centipoise (cp), flow is shown reducing to about 45% at a relative viscosity of 2500 cp. The flow reduction mimics a negative exponential pattern, with maximum reduction between viscosity values of 0 cp to about 500 cp. FIG. 5, which graphically depicts Head vs. viscosity, correspondingly reflects reduced pump head with increasing viscosity. It should be pointed out however a fluid's conditions can alter the effects a particular viscosity has on the fluid flow. For the purposes of discussion herein, a high viscosity therefore is not quantifiable in every situation, but instead a high viscosity can be defined where the fluid's resistance to flow can change the pumping system's operation or cause damage to the pumping system.

FIG. 6 graphically depicts the effect increasing viscosity has on pump Brake horse power (BHP) requirements; this correlation is useful in predicting pump start-up BHP. During pump start-up, wellbore fluid is generally at lower temperature and higher viscosity than during normal operation. As such, pump start-up BHP generally exceeds full speed BHP. Moreover, normal start-ups often involve the pump rotating at full operational speed from rest within a fraction of second. Pump shaft failure may therefore occur during start-up if the fluid is sufficiently viscous. For example, the increased start-up pump BHP may torque the pump shaft past its mechanical limits thereby causing shaft failure when pumping the liquid. However, by measuring fluid viscosity, pump BHP can be estimated prior to start-up and the pumping system operated at a motor output torque and speed to avoid surpassing shaft mechanical limits. In this situation, during pump start-up pump speed can be gradually increased up to operational speeds.

An additional application wherein wellbore fluid viscosity knowledge is useful involves heavy oil application, especially when the heavy oil is produced in conjunction with steam assisted gravity drainage (SAGD). Knowing the viscosity in heavy oil applications can be used for starting and stopping the pump which increases reliability. In a steam assisted gravity drainage (SAGD) of oil from sand oil application, fluid is heated by injection and mixed with steam. The viscosity information can be used to estimate a required heat energy input, a start time, and starting sequence.

An information handling system (IHS) may be employed for controlling and/or initiating monitoring commands herein described as well as receiving and/or controlling subsequent recording of any data monitored. Moreover, the IHS may also be used to store recorded data as well as processing the data into a readable format. The IHS may be disposed at the surface, in the wellbore, or partially above and below the surface. The IHS may include a processor, memory accessible by the processor, nonvolatile storage area accessible by the processor, and logics for performing each of the steps above described. The above described relationships can be programmed into the IHS and calculations performed using recorded data, such as viscosity data.

Often controlling a pumping system measures pump and/or motor performance and responds accordingly. This may cause drastic variations in pump speeds, especially when fluid viscosity is not constant. With changes in fluid properties, the pump motor speed can fluctuate before prompting adjustments in supplied power. Allowing such pump speed fluctuations reduces pumping system efficiency, and can cause pump failure. In contrast, knowing fluid conditions, as or prior to the fluid being pumped, pump speed and/or supplied power can be adjusted to maintain consistent pump speed thereby prolonging pump motor life.

Pump flow control may be modeled on the following relationships. Increasing fluid viscosity increases pump BHP, pump speed (RPM) is directly related to fluid flow through the pump. Pump head changes relate to flow changes squared and BHP cubed. To account for an increased viscosity RPM may be correspondingly reduced to reduce the BHP.

It is to be understood that the invention is not limited to the exact details of construction, operation, exact materials, or embodiments shown and described, as modifications and equivalents will be apparent to one skilled in the art. In the drawings and specification, there have been disclosed illustrative embodiments of the invention and, although specific terms are employed, they are used in a generic and descriptive sense only and not for the purpose of limitation. Accordingly, the invention is therefore to be limited only by the scope of the appended claims.

The invention claimed is:

1. A downhole submersible pumping system for use in a wellbore comprising:
   a pump in fluid communication with a fluid inlet;
   production tubing within the wellbore and having an end coupled to the pump;
   a pump motor coupled to the pump;

a viscometer;

a pumping system controller in communication with the viscometer; and a corrosion inhibitor injector selectively activated based on a measured viscosity value.

2. The downhole submersible pumping system of claim 1, wherein the system is disposed in a wellbore having fluid and the viscometer is in fluid communication with the fluid.

3. The downhole submersible pumping system of claim 2, wherein the viscometer is disposed at a location comprising a position selected from the list consisting of below the pump motor in the wellbore, adjacent the pump, adjacent the pump motor, proximate the pump intake.

4. The downhole submersible pumping system of claim 1, further comprising a communication link between the control system and the pump motor and a command signal in the communication link.

5. The downhole submersible pumping system of claim 1, further comprising an additional viscometer.

6. A method of operating a downhole submersible pumping system, the pumping system comprising a pump, production tubing disposed within the wellbore and having an end coupled to the pump, a pump motor coupled to the pump, a seal section, a pump inlet, a viscometer, a pumping system controller in communication with the viscometer, and a corrosion inhibitor injector selectively activated based on a measured viscosity value, the method comprising:

using the viscometer to measure fluid viscosity in a wellbore that is surrounded by a hydrocarbon producing formation, thereby obtaining a measured viscosity value;

controlling the pumping system with the pumping system controller in response to the measured viscosity value; and selectively activating the corrosion inhibitor injector based on the measured viscosity value.

7. The method of claim 6 further comprising estimating pump motor temperature based on the measured viscosity value.

8. The method of claim 6 further comprising controlling the pump motor based on the measured viscosity value.

9. The method of claim 8, wherein controlling the pump motor based on the measured viscosity value comprises an action selected from the list consisting of adjusting pump motor speed, adjusting pump motor torque, and adjusting power supplied to the pump motor.

10. The method of claim 6 further comprising estimating a control action using the controller based on of the measured viscosity value.

11. The method of claim 6 wherein the step of measuring fluid viscosity comprises disposing the viscometer in the wellbore.

12. The method of claim 11, wherein the viscometer is disposed at a location comprising a position selected from the list consisting of below the pump motor in the wellbore, adjacent the pump motor, and proximate the pump inlet.

* * * * *